United States Patent [19]
Mikolajczak et al.

[11] 3,959,312
[45] May 25, 1976

[54] SYNTHESIS OF ANTITUMOR ALKALOID DEOXYHARRINGTONINE AND ITS PRECURSOR 3'-O-(5-METHYL-2-OXOHEXANOYL)-CEPHALOTAXINE

[75] Inventors: Kenneth L. Mikolajczak, Benson; Cecil R. Smith, Jr., Dunlap, both of Ill.

[73] Assignee: The United States of America as represented by the Secretary of Agriculture, Washington, D.C.

[22] Filed: Dec. 20, 1974

[21] Appl. No.: 534,925

[52] U.S. Cl. .......................... 260/326.29; 424/274
[51] Int. Cl.² ...................................... C07D 491/14
[58] Field of Search ............................... 260/326.29

[56] References Cited
UNITED STATES PATENTS 3,870,727   3/1975   Powell et al. ................. 424/279 X

*Primary Examiner*—Alton D. Rollins
*Assistant Examiner*—Mark L. Berch
*Attorney, Agent, or Firm*—M. Howard Silverstein; Max D. Hensley; David G. McConnell

[57] ABSTRACT

The alkaloid deoxyharringtonine and its precursor 3'-O-(5-methyl-2-oxohexanoyl)-cephalotaxine were synthesized according to the following preferred series of reactions: Ethyl t-butyl oxalate + 1-lithio-3-methylbut-1-yne ⟶ t-butyl 5-methyl-2-oxohex-3-ynoate ⟶ t-butyl 5-methyl-2-oxohexanoate —$\textit{trifluoroacetic acid}$→ 5-methyl-2-oxohexanoic acid —$\textit{(COCl)}$→ 5-methyl-2-oxohexanoyl chloride —$\textit{cephalotaxine}$→ 3'-O-(5-methyl-2-oxohexanoyl)-cephalotaxine —$\textit{lithio methyl acetate}$→ deoxyharringtonine.

4 Claims, 6 Drawing Figures

FIG. 5 HIGH-RESOLUTION MASS SPECTRUM OF SYNTHETIC DEOXYHARRINGTONINE

SYNTHESIS OF ANTITUMOR ALKALOID DEOXYHARRINGTONINE AND ITS PRECURSOR 3'-0-(5-METHYL-2-OXOHEXANOYL)-CEPHALOTAXINE

BACKGROUND OF THE INVENTION

This invention relates to synthesis of an alkaloid which is active against lymphocytic leukemia in test mice. It further relates to the synthesis of deoxyharringtonine and its precursor 3'-O-(5-methyl-2-oxohexanoyl)-cephalotaxine.

Among the alkaloids which have been isolated from *Cephalotaxus harringtonia* plant material are cephalotaxine and a number of its esters [Powell, Weisleder, Smith, and Wolff, Tetrahedron Lett. 4081 (1969); Powell, Weisleder, Smith, and Rohwedder, Tetrahedron Lett. 815 (1970); and Mikolajczak et al., Tetrahedron 28: 1995 (1972)]. Some of these esters, which are derived from relatively complex dicarboxylic acid moieties have been found to exhibit significant antitumor activity in the P388 system [cephalotaxine itself is inactive; Powell et al., J. Pharm. Sci. 61: 1227 (1972)]. Two of the esters have been approved for the preclinical phase of pharmacological evaluation at the National Cancer Institute. Continued biological testing of the active esters requires quantities which cannot be supplied by natural sources. The partial synthesis of these esters from natural and synthetic cephalotaxine which is available in considerably larger quantities is very desirable. We have discovered a successful conversion of cephalotaxine to one of its active naturally occurring esters, deoxyharringtonine.

DETAILED DESCRIPTION OF THE INVENTION

Figure 1:
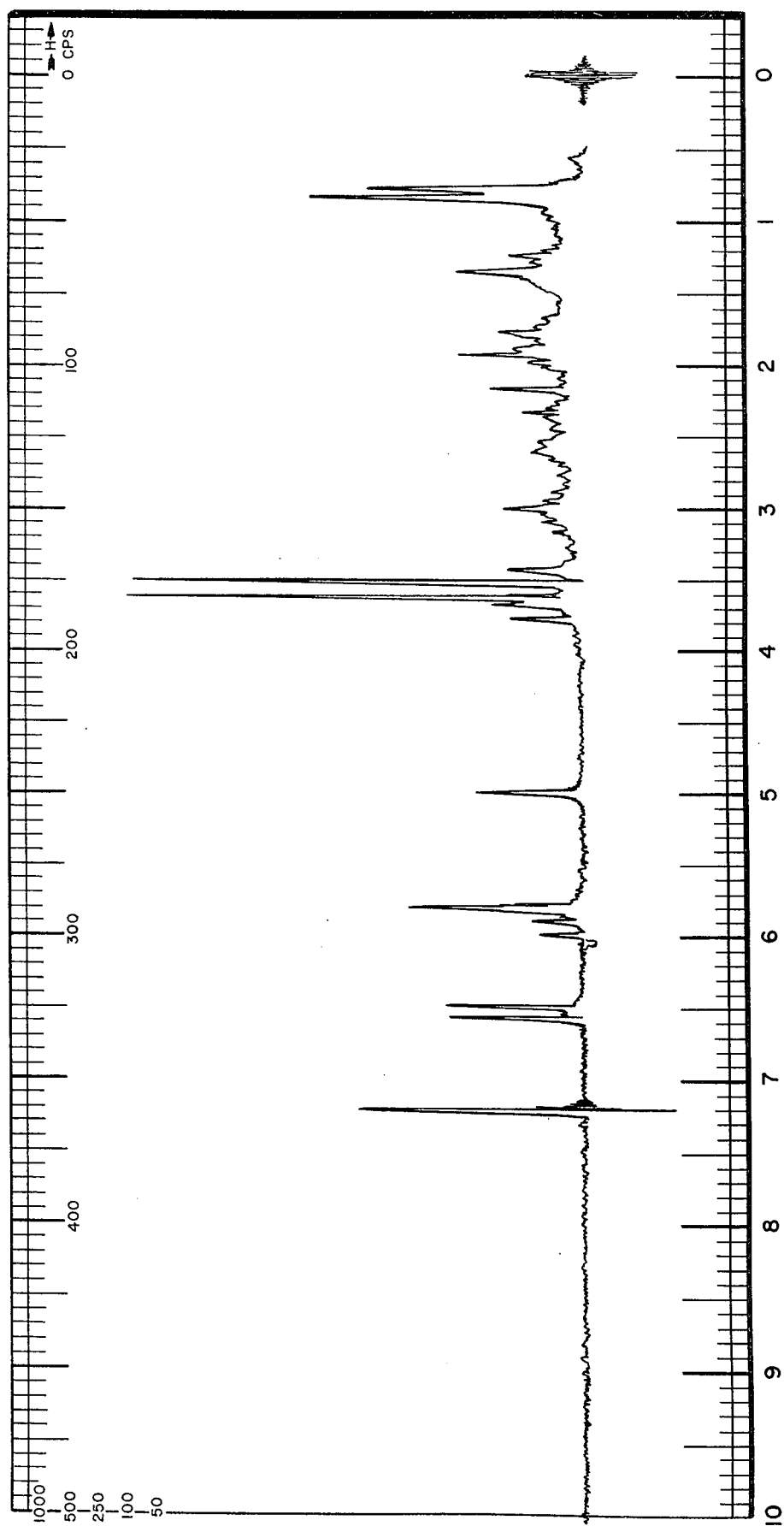
FIGS. 1, 3, and 5 consist, respectively, of a nuclear magenetic resonance spectrum, an infrared absorption spectrum, and a high resolution mass spectrum of synthetic deoxyharringtonine.

Step (a) Synthesis of 1 (i.e., t-butyl 5-methyl-2-oxohex-3-ynoate)

Ethyl t-butyl oxalate

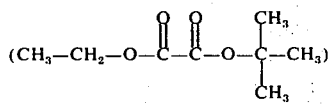

can be prepared by the method of Carpino [J. Amer. Chem. Soc. 82: 2725 (1960)], and 1-lithio-3-methylbut-1-yne

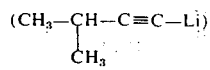

can be prepared by reacting commercially available 3-methylbut-1-yne and n-butyllithium under anhydrous conditions in an inert atmosphere (i.e., no $H_2O$, $O_2$, or $CO_2$) at a temperature of from 0° to 5° C. Anhydrous tetrahydrofuran (THF) is the preferred solvent for the reactions of step (a).

Since lithium compounds are not sufficiently soluble in THF, it is necessary to add a small amount of a low molecular weight hydrocarbon solvent to the reaction media. Low molecular weight hydrocarbon solvents suitable for dissolving the lithium compounds used herein include pentane, hexane, heptane, octane, and petroleum ether. The preferred amount of these solvents is the minimum required to solvate the desired lithium compound in THF. This is easily determined by anyone skilled in the art.

Reaction (1), infra, is carried out in THF under strict anhydrous conditions, in an inert atmosphere, at temperatures of from 0° to 10° C.:

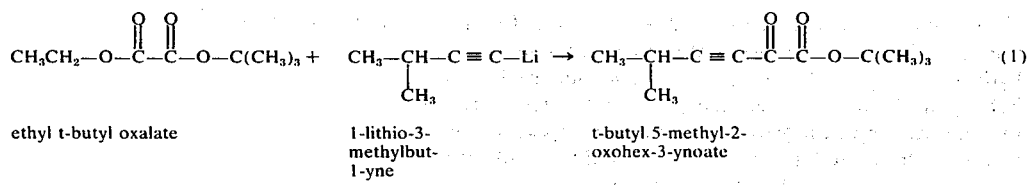

| ethyl t-butyl oxalate | 1-lithio-3-methylbut-1-yne | t-butyl 5-methyl-2-oxohex-3-ynoate |

In order to prevent yield decreasing side reactions, it is preferred that ethyl t-butyl oxalate be in excess of the stoichiometric amount at all times during the reaction. Therefore, 1-lithio-3-methylbut-1-yne is preferably added slowly to the oxalate, and ethyl t-butyl oxalate is preferably present in from 150% to 165% excess of the stoichiometric amount. Theoretically, there is no upper limit to the excess over stoichiometry of the oxalate in reaction (1). For the sake of simplicity, all reactions shown herein include only the major reactants and products. No attempt was made to show balanced reactions.

t-Butyl 5-methyl-2-oxohex-3-ynoate can be recovered by adding water to the reaction mixture and extracting with a suitable organic solvent such as diethyl ether, hexane, or petroleum ether. However, yields are diminished unless the basic reaction mixture is quenched preferably with aqueous pH 7 buffer rather than water prior to extraction by the organic solvent. The desired product can then be purified by distilling off excess ethyl t-butyl oxalate present in the extract followed by purification of the t-butyl 5-methyl-2-oxohex-3-ynoate by elution from a silica gel column. However, the pot residue after removing excess ethyl t-butyl oxalate is suitable for use in the next step without further processing.

Step (b) Synthesis of 1a (i.e., t-butyl 5-methyl-2-oxohexanoate)

Hydrogenation of t-butyl 5-methyl-2-oxohex-3-ynoate to t-butyl 5-methyl-2-oxohexanoate is accomplished by reaction (2) with gaseous hydrogen with a catalytic amount of a suitable catalyst such as metallic palladium, platinum, nickel, their oxides, or their salts.

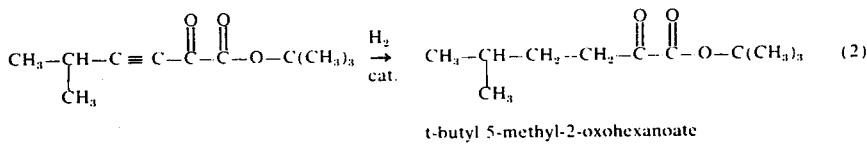

t-butyl 5-methyl-2-oxohexanoate

Step (c) Synthesis of 5-Methyl-2-oxohexanoic Acid t-Butyl 5-methyl-2-oxohexanoate is readily hydrolyzed under suitably mild conditions at room temperature (i.e., 25°–30° C.). Suitable reactions include hydrolysis directly to the acid form using trifluoroacetic acid [reaction (3)] or hydrolysis with dilute bases such as sodium or potassium hydroxide followed by acidification with dilute mineral acids such as hydrochloric, sulfuric, or nitric acids.

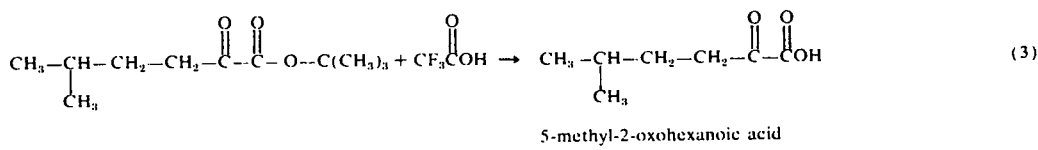

5-methyl-2-oxohexanoic acid

Trifluoroacetic acid can be used as a solvent for the reaction shown (3). When trifluoroacetic acid is the hydrolyzing reagent, this step can be accomplished before the hydrogenation step. The acid is recovered by volatization of the trifluoroacetic acid. If hydrolysis is done with dilute base, followed by acidification with mineral acid, the acid is then extracted in the same manner as described for the extraction of the ester in step (a).

Step (d) Preparation of 2 Acid Chloride (i.e., 5-methyl-2-oxohexanoyl chloride)

The 5-methyl-2-oxohexanoic acid is reacted with at least a 10% excess over the stoichiometric amount of oxalyl chloride to form 5-methyl-2-oxohexanoyl chloride [reaction (4)].

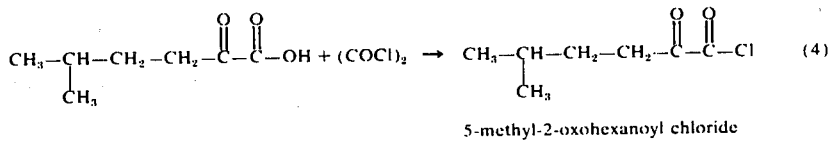

5-methyl-2-oxohexanoyl chloride

Oxalyl chloride is a suitable solvent for reaction (4), and theoretically can be present in an unlimited excess over stoichiometry. Solvents such as diethyl ether, petroleum ether, benzene, $CH_2Cl_2$, and hexane are also suitable solvents for the reaction. The use of solvents is preferred but is not necessary. Reaction (4) must be run under anhydrous conditions in an inert atmosphere and requires from 40 to 60 hours at a temperature of from 25° to 60° C. for completion.

Step (3) Preparation of 3b [i.e., 3'-O-(5-methyl-2-oxohexanoyl)-cephalotaxine]

Reaction (5), infra, involves the addition of 5-methyl-2-oxohexanoyl chloride to cephalotaxine to form intermediate compound 3b.

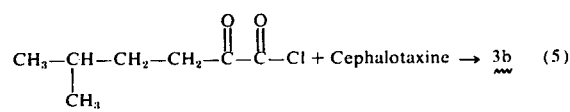

3'-O-(5-methyl-2-oxohexanoyl)-cephalotaxine has the following structure:

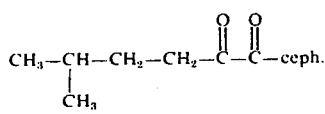

where -ceph. has the following structure:

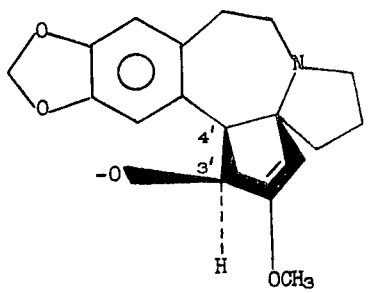

Natural cephalotaxine (Powell et al., supra) and synthetic cephalotaxine identical to the natural material [Auerbach et al., J. Amer. Chem. Soc. 94: 7172 (1972); Semmelhack et al., J. Amer. Chem. Soc. 94: 8629 (1972); and Semmelhack, Stauffer, and Rogerson, Tetrahedron Lett. 4519 (1973)] are equivalent for the purposes of this invention. Reaction (5) is carried out under anhydrous conditions in a suitable solvent which will solubilize and at the same time will be inert to the reactants (e.g., THF, $CH_2Cl_2$, or $CHCl_3$) and at room temperature (25°–30° C.) for a minimum of 24 hours in the presence of pyridine. Pyridine should be present in equal molar quantities with the acid chloride. It is preferred that the acid chloride starting material be present in the reaction mixture from 50% to 200% excess of the stoichiometric amount. However, there is no theoretical limit to the excess amount of the acid chloride. It is understood that reaction temperatures over 25° C. reduce the time of reaction and that the reaction can be allowed to proceed greatly beyond 24 hours at room temperature with little detrimental effect on the product or the yield.

3'-O-(5-Methyl-2-oxohexanoyl)-cephalotaxine was isolated by simple extraction with chloroform followed by the removal of solvents by distillation under vacuum. The product can be purified by column chromatography or equivalent procedure and is suitable as such for use in the next step of the synthesis. However, due to its rather low stability, it is preferred that the crude pot residue product be used without further purification.

Step (f) Preparation of Deoxyharringtonine

Conversion of 3b to deoxyharringtonine is accomplished by reaction with lithio methyl acetate [reaction (6)].

from −65° to −75° C., and adding to the reaction mixture 3b and methyl acetate in THF.

The mixture of deoxyharringtonine and 3d is easily isolated by simple extraction, such as that described for the recovery of t-butyl 5-methyl-2-oxohex-3-ynoate in step (a), supra.

Step (g) Separation of Deoxyharringtonine and 3d

Laboratory sized samples of the diastereomer mixture from step (f) were subjected to thin-layer chromatography (tlc) on commercially available 2-mm. silica gel plates using a solvent system consisting of 20% methanol in benzene. The material obtained from this tlc was further fractionated on 0.25-mm. silica gel plates with the same solvent system. Essentially pure deoxyharringtonine (99%) and 3d (95%) were obtained in this manner. Other methods suitable for the separation of deoxyharringtonine from 3d include column chromatography and counter-current distribution.

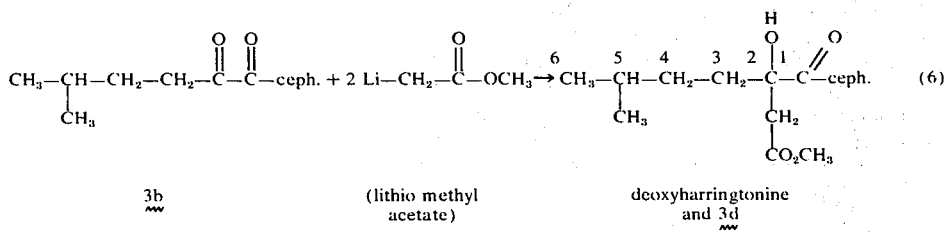

```
    3b              (lithio methyl           deoxyharringtonine
                      acetate)                   and 3d
```

Reaction (6), supra, generates a new asymmetric center on carbon No. 2 of the reaction product which is a mixture of deoxyharringtonine and its diastereoisomer (3d).

Diastereoisomers (i.e., diastereomers) are defined herein as being inversional isomers that have identical structural configurations about all corresponding nonasymmetric carbons and about all corresponding asymmetric carbons except one. Deoxyharringtonine and 3d are diastereomers which are identical except that the structural configuration about carbon No. 2 is inverted.

Figure 2:
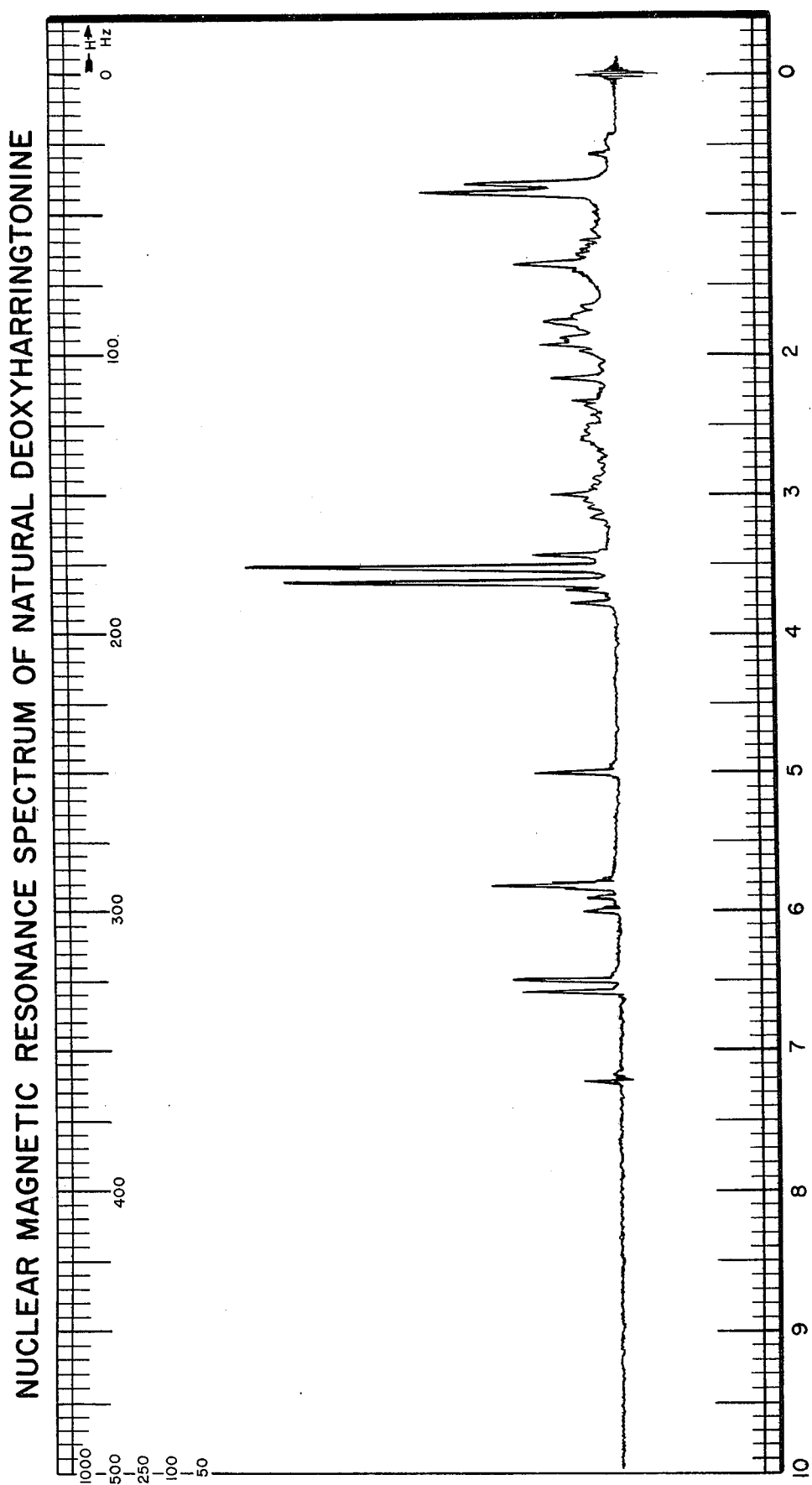
FIGS. 2, 4, and 6 consist, respectively, of a nuclear magnetic resonance spectrum, an infrared absorption spectrum, and a high resolution spectrum of natural deoxyharringtonine.
Figure 3:
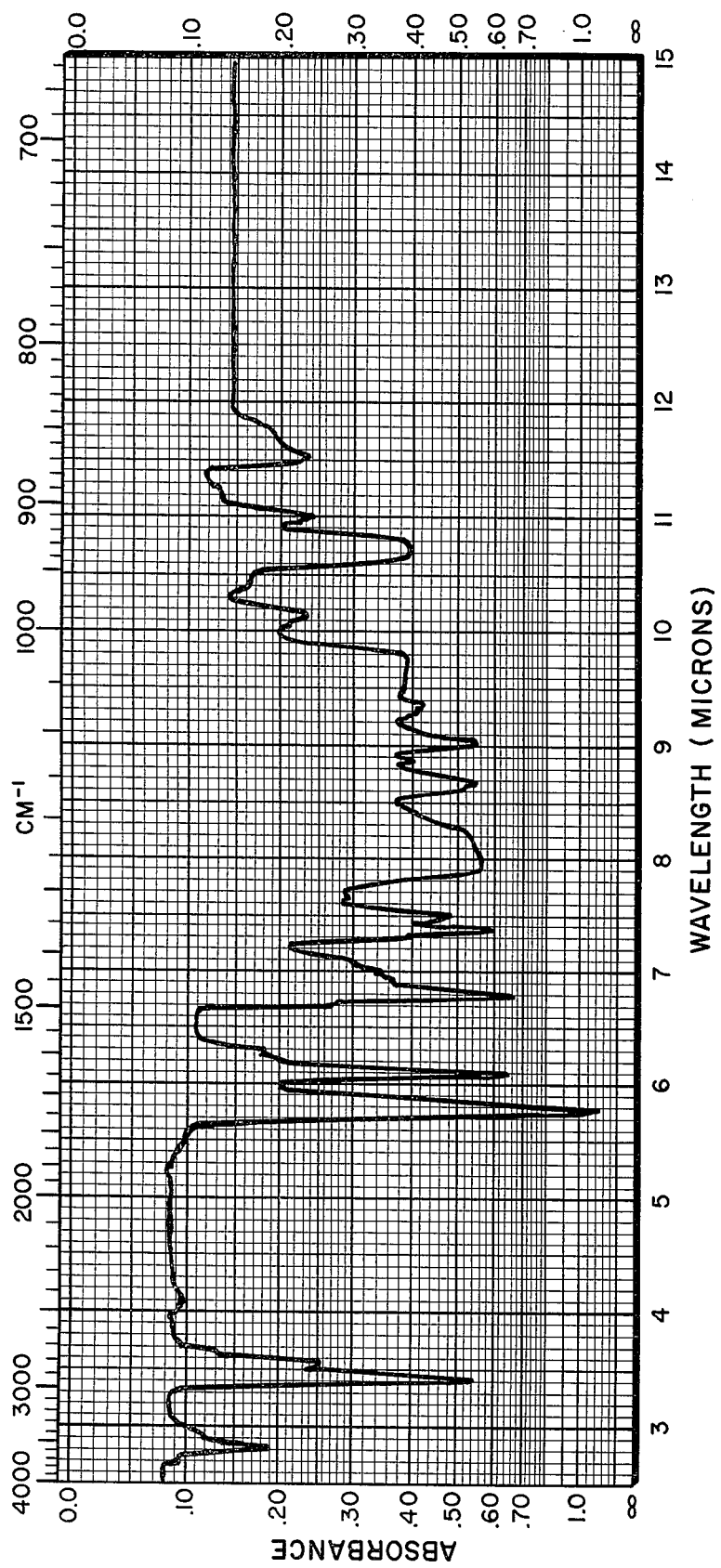
Figure 4:
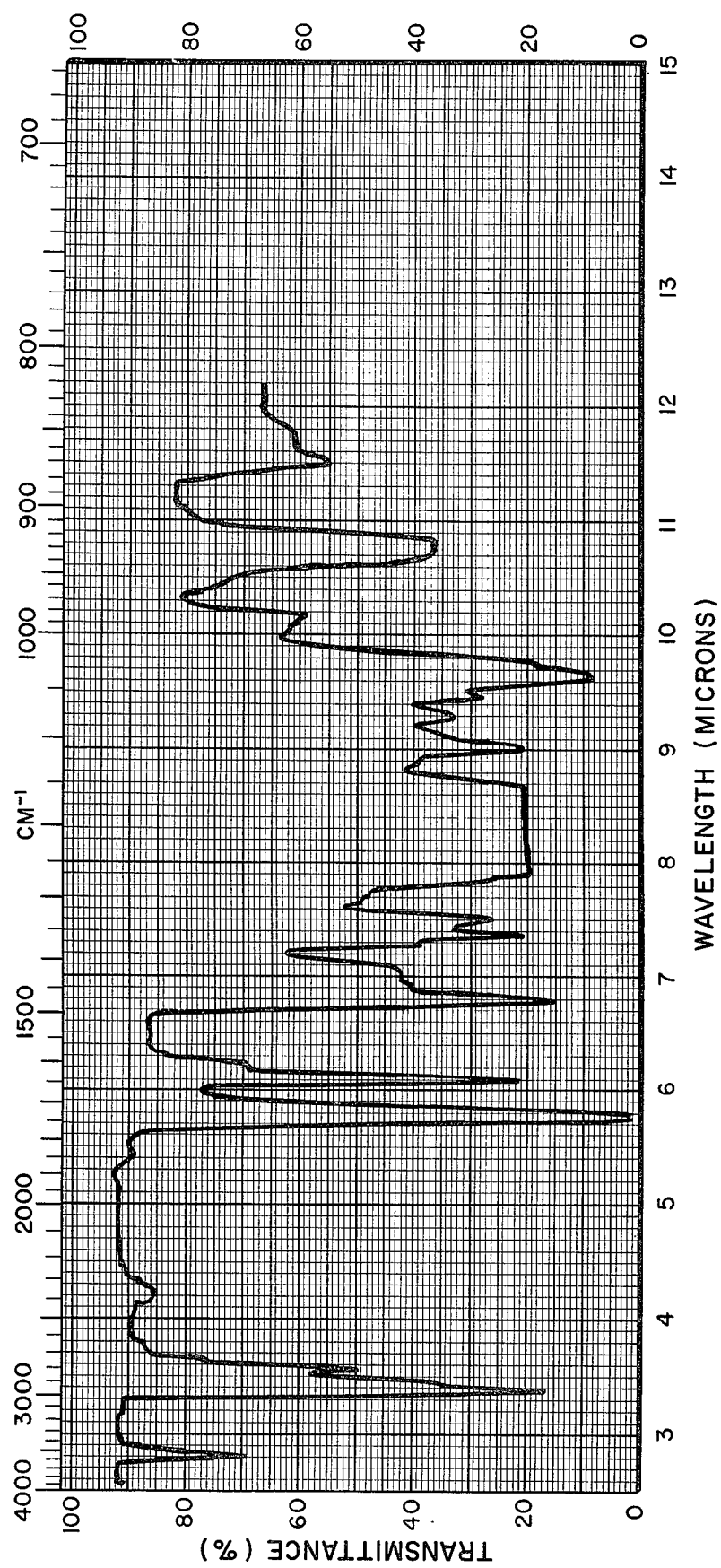
Figure 5:
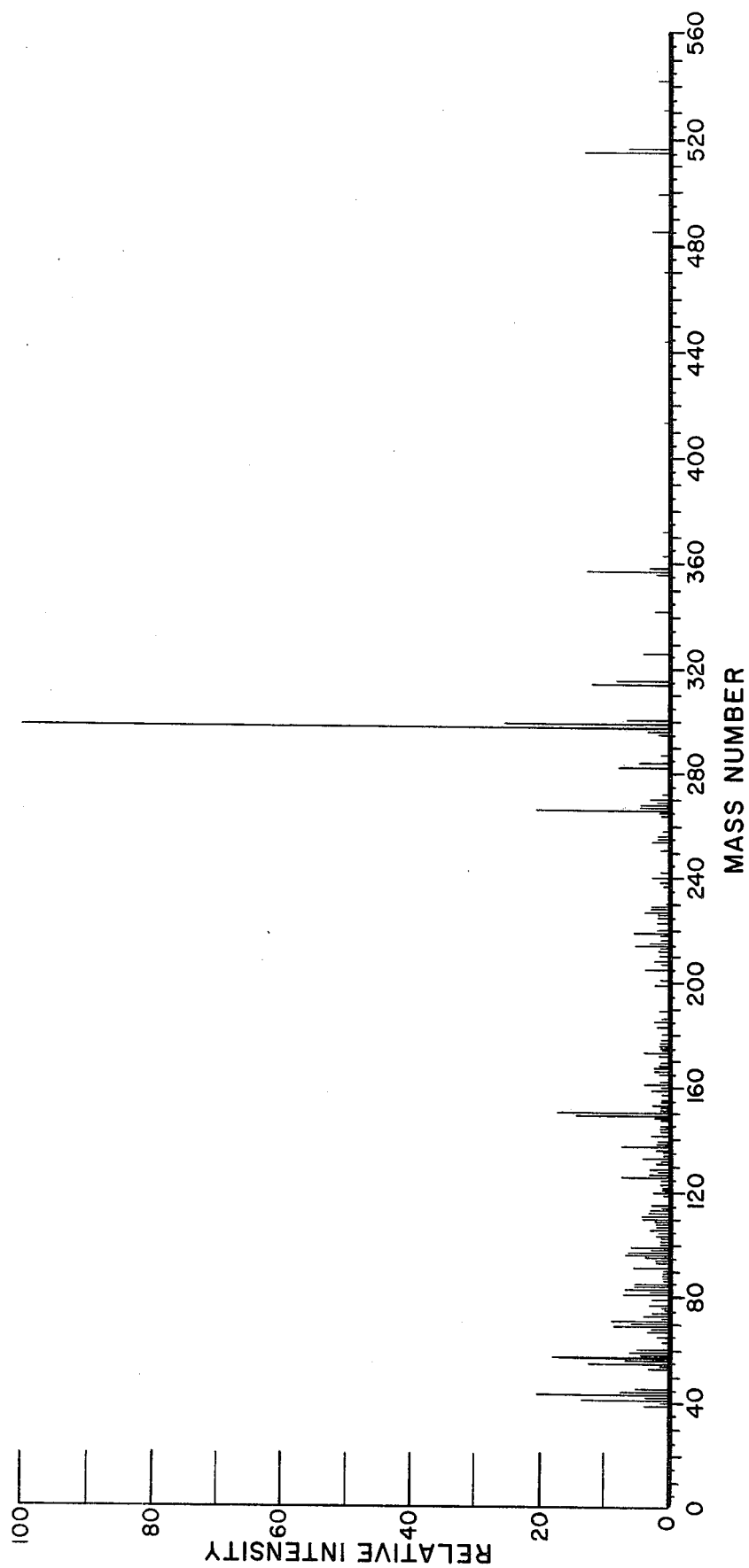
Figure 6:
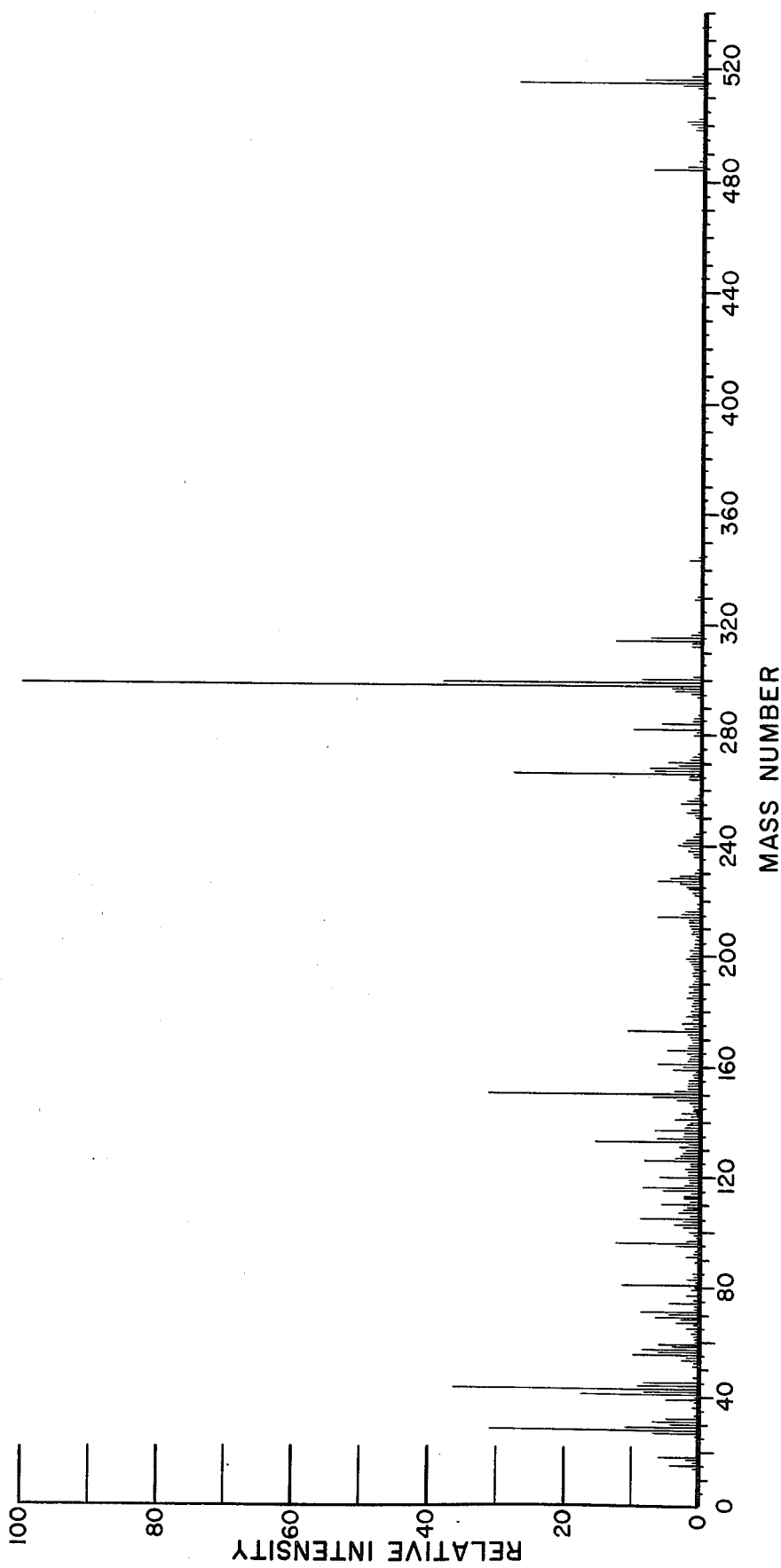

Lithio methyl acetate was prepared from two equivalents of lithium isopropyl cyclohexylamide and about two equivalents of methyl acetate at from −65° to −75° C. under anhydrous conditions in an inert atmosphere [Rathke et al., J. Amer. Chem. Soc. 93: 2318 (1971)]. Preferably, because of the high reactivity of lithio methyl acetate, reaction (6) is accomplished by first preparing the lithium isopropyl cyclohexylamide from isopropyl cyclohexylamine and n-butyllithium at about 0° C. under anhydrous conditions in an inert atmosphere and an inert solvent, cooling the solution to The 100 MHz nmr and the ir spectra of deoxyharringtonine (FIGS. 1 and 3 of the drawings, respectively) synthesized in accordance with the invention match exactly the corresponding spectra of natural deoxyharringtonine (FIGS. 2 and 4 of the drawings, respectively). The results of mass spectrographic analysis also show that synthetic (FIG. 5 of the drawings) and natural (FIG. 6 of the drawings) deoxyharringtonine are the same compound. However, as shown in the following table, the nmr spectrum of 3d is different than those of synthetic and natural deoxyharringtonine.

Natural deoxyharringtonine is known to be useful as a tumor inhibitor in the lymphocytic leukemia P388 system in experimental mice (Powell et al., supra). Results of Example 3 show that deoxyharringtonine prepared in accordance with the invention is also active in the same system.

The following examples are intended only to further describe the invention and are not to be construed as limiting the scope of the invention as defined in the claims, infra.

| | | Deoxyharringtonine | |
|---|---|---|---|
| Protons of: | Synthetic (3c) | Natural | 3d |
| Isopropyl group | δ 0.81 (d, J=6 Hz, 6H) | δ 0.81 (d, J=6 Hz, 6H) | δ 0.75 (d, J=6 Hz, 6H) |
| —CH$_2$CO$_2$CH$_3$ | δ 1.86, 2.26 (dd, J=16 Hz, 2H) | δ 1.86, 2.26 (dd, J=16 Hz, 2H) | δ 2.46, 2.66 (dd, J=17 Hz, 2H) |
| —OCH$_3$ | ⎧ δ 3.53 (s, 3H) <br> ⎩ δ 3.64 (s, 3H) | ⎧ δ 3.53 (s, 3H) <br> ⎩ δ 3.64 (s, 3H) | ⎧ δ 3.60 (s, 3H) <br> ⎩ δ 3.62 (s, 3H) |
| C-4'[1] | δ 3.73 (d, J=10 Hz, 1H) | δ 3.73 (d, J=10 Hz, 1H) | δ 3.72 (d, J=10 Hz, 1H) |
| Vinyl | δ 5.01 (s, 1H) | δ 5.01 (s, 1H) | δ 4.99 (s, 1H) |
| —O—CH$_2$—O— | δ 5.82 (br s, 2H) | δ 5.82 (br s, 2H) | δ 5.82 (br s, 2H) |
| C-3'[1] | δ 5.96 (d, J=10 Hz, 1H) | δ 5.96 (d, J=10 Hz, 1H) | δ 5.86 (d, J=10 Hz, 1H) |
| Aromatic | ⎧ δ 6.50 (s, 1H) <br> ⎩ δ 6.59 (s, 1H) | ⎧ δ 6.50 (s, 1H) <br> ⎩ δ 6.59 (s, 1H) | δ 6.56 (s, 2H) |

[1]Ceph. carbons.

EXAMPLE 1 a. t-Butyl 5-methyl-2-oxohex-3-ynoate. The 1-lithio-3-methylbut-1-yne starting material was prepared as follows: a solution of 15 ml. of anhydrous THF, 0.050 g. of triphenylmethane and 2.10 g. of 3-methylbut-1-yne was cooled in an ice-water bath at 0° C. To this was added a 2.2 M solution of n-butyllithium in hexane at a rate which allowed the temperature of the THF solution to remain between 0° and 5° C., until the solution turned an orange-red color. Stirring at 0° to 5° C. continued 20 minutes after the last addition of the hexane solution to the THF solution. This reaction was done under anhydrous conditions in an inert dry-nitrogen atmosphere.

Air, moisture, and $CO_2$ were excluded from the reaction by first passing nitrogen through a dry silica gel column before bubbling through the reaction mixture. The resulting 1-lithio-3-methylbut-1-yne solution at 0° to 5° C. was added to a 15-ml. anhydrous THF solution containing 5 ml. anhydrous hexane and 13.0 g. ethyl t-butyl oxalate at a rate which allowed the resulting reaction mixture to remain at a temperature of from 0° to 10° C. Stirring of the above reaction mixture was continued for 20 minutes after final addition of the 1-lithio-3-methylbut-1-yne solution. To this solution was added 50 ml. of a pH 7 buffer (1.184 g. NaOH, 6.800 g. $KH_2PO_4$, diluted to 1 liter with $H_2O$). The mixture was then extracted four times with 100 ml. of diethyl ether, the ether extracts combined, and the ether removed. Excess ethyl t-butyl oxalate was removed by distillation under 3 to 4 mm. of mercury at 57° to 61° C. The pot residue was chromatographed on a 2.5 × 30 cm. silica gel column. A first elution of 100 ml. of petroleum ether (b.p. 30°–60° C.) followed by 400 ml. of a solution of 3% diethyl ether in petroleum ether eluted the essentially pure t-butyl 5-methyl-2-oxohex-3-ynoate in a 1.495-g. yield which was 23.4% of theory based on 3-methylbut-1-yne.

A 1% solution of the product in chloroform ($CHCl_3$) analyzed by a Perkin-Elmer Model 137 spectrophotometer gave ir bands at 2210 cm$^{-1}$ (conjugated —C≡C—), 1730 cm$^{-1}$ (ester —C=O), and 1670 cm$^{-1}$ ($\alpha,\beta$-unsaturated —C=O). Nmr spectra obtained on $CDCl_3$ solutions with a Varian HA-100 spectrometer gave chemical shifts relative to internal TMS of $\delta$ 1.26 (d, J = 7 Hz, 6H, isopropyl), $\delta$ 1.53 (s, 9H, $CH_3$— of t-butyl group), and $\delta$ 2.78 (septet, J = 7 Hz, 1H, methine proton).

b. t-Butyl 5-methyl-2-oxohexanoate. t-Butyl 5-methyl-2-oxohex-3-ynoate (0.430 g.) was dissolved in 10 ml. of hexane and hydrogenated at 25° to 30° C. with hydrogen at atmospheric pressure and 0.035 g. palladium on charcoal catalyst until hydrogen uptake ceased. Filtration to remove catalyst and removal of the solvent from the hydrogenation mixture resulted in a quantitative yield (0.430 g.) of the saturated $\alpha$-keto ester product which showed no ir bands at 2210 or 1670 cm$^{-1}$.

c. 5-Methyl-2-oxohexanoic acid. The saturated $\alpha$-keto ester (0.430 g.) from step (b) was stirred with 2 ml. of trifluoroacetic acid for 45 minutes at 0° C. Removal of excess reagent under vacuum resulted in a quantitative yield (0.310 g.) of 5-methyl-2-oxohexanoic acid; ir (1%, $CHCl_3$): 2700–3600 cm$^{-1}$ (broad, free —COOH), and 1720 and 1780 cm$^{-1}$ (2 —C=O bands of equal intensity); nmr ($CDCl_3$, 100 MHz): $\delta$ 0.91 (d, J = 7 Hz, 6H, isopropyl), $\delta$ 1.55 (very broad t, principle J = 7 Hz, 2H, methylene adjacent to isopropyl), $\delta$ 2.37 (indistinct multiplet, principle J = 7 Hz, 1H, methine), $\delta$ 2.89 (t, J = 7 Hz, 2H, methylene $\alpha$ to —C=O), and $\delta$ 8.26 (broad s, 1H, carboxyl).

d. 5-Methyl-2-oxo-hexanoyl chloride. The 5-methyl-2-oxohexanoic acid (0.310 g.) from step (c) was reacted with 2 ml. of oxalyl chloride in 5 ml. of anhydrous diethyl ether for 40 hours at about 25° C. Anhydrous conditions were maintained as in step (a). Excess oxalyl chloride and solvent were removed in vacuo. The resulting product (0.340 g.) was used in the next step without further processing.

e. 3'-O-(5-methyl-2-oxohexanoyl)-cephalotaxine. The acid chloride product (0.340 g.) from step (d) was dissolved in 3 ml. of methylene chloride ($CH_2Cl_2$) and added to 0.500 g. of natural cephalotaxine (Powell et al., supra) and 1 ml. of pyridine in 3 ml. $CH_2Cl_2$. The reaction was stirred at about 25° C. for 24 hours, after which 15 ml. of 5% aqueous $Na_2CO_3$ was added and the mixture extracted three times with 25 ml. $CH_2Cl_2$, the extract washed once with 10 ml. of distilled water, dried over anhydrous $MgSO_4$, and the solvent evaporated under vacuum. The crude product (0.568 g.) was estimated by tlc analysis to be from 60 to 80% 3'-O-(5-methyl-2-oxohexanoyl)-cephalotaxine. Tlc analysis was done on Brinkmann precoated 0.25-mm. F-254 plates with 15% methanol in chloroform, and the spots were visualized by staining with iodine vapor.

The remainder was cephalotaxine. The crude product gave: ir (1%, $CHCl_3$): 1725 cm$^{-1}$ with a strong shoulder at 1730 cm$^{-1}$ (ester —C=O, plus $\alpha$-keto group), 1645 cm$^{-1}$ (vinyl of cephalotaxine), and 935 cm$^{-1}$ (—OCH$_2$O—); nmr ($CDCl_3$, 100 MHz): $\delta$ 0.81 (d, J = 6 Hz, 6H, isopropyl), $\delta$ 3.68 (s, 3H, —$OCH_3$), $\delta$ 3.81 (d, J = 10 Hz, 1H, C-4' cephalotaxine proton), $\delta$ 5.08 (s, 1H, vinyl), $\delta$ 5.82 (s, 2H, —$OCH_2O$—), $\delta$ 5.86 (d, J = 10 Hz, 1H, C-3' cephalotaxine proton), and $\delta$ 6.56 and $\delta$ 6.58 (2s, 1H each, aromatic protons).

High resolution mass spectral analysis of the product gave M$^+$ = 441.215; $C_{25}H_{31}NO_6$ requires 441.215.

f. Deoxyharringtonine. A solution of 0.368 ml. of anhydrous isopropylcyclohexylamine in 5 ml. of THF was cooled to 0° C. in an ice-water bath with stirring. While this solution was being vigorously stirred, 1.25 ml. of 2.2 M n-butyllithium in n-hexane was added at a rate which kept the temperature between 0° and 5° C. Stirring was continued for 30 minutes after the last addition of the n-butyllithium solution. Throughout the reaction anhydrous nitrogen was used to exclude air, moisture, and $CO_2$ from the reaction vessel. The reaction medium was then cooled to −75° C. in a dry ice-ethanol bath. An anhydrous solution of 0.473 g. of 3'-O-(5-methyl-2-oxohexanoyl)-cephalotaxine, 0.170 ml. of methyl acetate, and 5 ml. of THF was added at a rate sufficient to keep the reaction temperature between −75° and −65° C. (i.e., total addition time about 30 minutes). Stirring was continued after final addition for 1.5 hours at −75° C. The solution was allowed to warm to room temperature (25°–30° C.) and stirred an additional 30 minutes, after which it was poured into 50 ml. of pH 7 buffer [see step (a)] and extracted three times with 40 ml. of $CHCl_3$. The extract was dried over anhydrous $MgSO_4$ and the solvent removed. The crude product (0.458 g.) contained two diastereoisomers; deoxyharringtonine (identical with the natural product) and a diastereomer of deoxyharringtonine plus unesterified cephalotaxine.

g. Purification of deoxyharringtonine. Preliminary concentration of the crude product resulting from step (f) was achieved by applying the crude product to Brinkmann 2-mm. silica gel F-254 thin-layer plates and developing the plates with a solution of 20% methanol in benzene. They were visualized by spraying them with an ethanolic solution of bromothymol blue. Deoxyharringtonine had an $R_f$ value of 0.55 while the diastereomer of deoxyharringtonine had an $R_f$ value of 0.49. The silica gel containing the diastereoisomers was removed from the plate, extracted with 20% methanol in chloroform, filtered; the filtrate was washed once with 15 ml. of 5% aqueous $Na_2CO_3$ solution. The concentrated product was applied to Brinkmann 0.25-mm. silica gel F-254 thin-layer plates which were then subjected to double development by a solution of 20% methanol in benzene and visualized by bromothymol blue spray reagent. The silica gel containing deoxyharringtonine and that containing the diastereomer of deoxyharringtonine were separately extracted with 20% methanol in chloroform and the two compounds recovered. Yields based on the α-keto ester of cephalotaxine were 6% of 99% pure deoxyharringtonine and 9% of 95% pure diastereomer of deoxyharringtonine. Both compounds were analyzed as 1% solutions in $CHCl_3$ by ir in 1-mm. NaCl cells, by 100 MHz nmr, and by high-resolution mass spectrometry (see FIGS. 1–6).

EXAMPLE 2

Example 1 was repeated with the exception that the pot residue resulting from step (a) was not purified by silica gel column chromatography but was hydrogenated in the crude form in step (b). The final products were isolated in yields of 7.0% for deoxyharringtonine and 9.5% for the diastereomer of deoxyharringtonine.

EXAMPLE 3

Deoxyharringtonine prepared as in Example 1 was tested against lymphocytic leukemia P388 in $BDF_1$ mice in accordance with protocol 1.200, Cancer Chemotherapy Reports, Part 3, Vol. 3, No. 2, September 1972, Protocols for Screening Chemical Agents and Natural Products Against Animal Tumors and Other Biological Systems, 3rd ed., U.S. Department of Health, Education, and Welfare, DHEW Publication No. (NIH) 73-22. Treated mice were each injected intraperitoneally once a day with a total of nine injections in a multidose assay. Evaluations of the test animals (T) and of the control animals (C) were made according to protocol 11.200 Cancer Chemotherapy Reports, supra (Median Survival Time), and percent survival time (T/C) was calculated. The product is considered to be active if one or more dose levels result in a T/C of ≥ 125%. The following table shows the results of the multidose assay of deoxyharringtonine.

| Dose, mg./kg. of animal wt./inj. | Toxicity day survivors T | C | Animal wt. difference T-C, g. | Tumor evaluation T | C | T/C, % |
|---|---|---|---|---|---|---|
| 13.0 | 5 | 6 | −1.4 | 6.8 | 11.4 | — |
| 9.0 | 5 | 6 | −2.0 | 7.0 | 11.4 | — |
| 5.9 | 6 | 6 | −0.9 | 21.0 | 11.4 | 184 |
| 4.0 | 6 | 6 | 0.0 | 22.0 | 12.6 | 174 |
| 2.0 | 6 | 6 | 0.8 | 16.0 | 12.6 | 126 |
| 1.0 | 6 | 6 | 0.2 | 13.3 | 12.6 | 105 |
| 0.5 | 6 | 6 | 1.2 | 14.3 | 12.6 | 113 |

We claim:

1. A process for the preparation of deoxyharringtonine comprising the steps of:

a. reacting 3-O-(5-methyl-2-oxohexanoyl)-cephalotaxine with lithio methyl acetate in a molar ratio of 1:2 3-O-(5-methyl-2-oxohexanoyl)-cephalotaxine:lithio methyl acetate in THF under anhydrous conditions, in an inert atmosphere, at −78° C. to form a mixture of deoxyharringtonine and a deoxyharringtonine diastereomer; and b. separating deoxyharringtonine from the mixture resulting from step (a).

2. A process for the preparation of deoxyharringtonine comprising the steps of:

a. reacting 1-lithio-3-methylbut-1-yne with a 150% to 165% excess of the stoichiometric amount of ethyl t-butyl oxalate in THF containing an amount of a suitable hydrocarbon solvent sufficient to solubilize said 1-lithio-3-methylbut-1-yne, the reaction being carried out under anhydrous conditions in an inert atmosphere at a temperature of from 0° to 10° to form t-butyl 5-methyl-2-oxohex-3-ynoate;

b. hydrogenating t-butyl 5-methyl-2-oxohex-3-ynoate in the presence of a catalytic amount of a suitable catalyst to form t-butyl 5-methyl-2-oxohexanoate;

c. hydrolyzing t-butyl 5-methyl-2-oxohexanoate under mild conditions to form 5-methyl-2-oxohexanoic acid;

d. reacting 5-methyl-2-oxohexanoic acid with at least a 10% excess of the stoichiometric amount of oxalyl chloride under anhydrous conditions at a temperature of 25° to 60° C. for from 40 to 60 hours to form 5-methyl-2-oxohexanoyl chloride;

e. reacting cephalotaxine with a 50% to 200% excess of the stoichiometric amount of 5-methyl-2-oxohexanoyl chloride in a suitable solvent at about 25° to 30° C. for a minimum of 24 hours in the presence of a molar amount of pyridine equivalent to the initial amount of 5-methyl-2-oxohexanoyl chloride to form 3'-O-(5-methyl-2-oxohexanoyl)-cephalotaxine;

f. reacting 3'-O-(5-methyl-2-oxohexanoyl)-cephalotaxine contained in the reaction mixture resulting from step (e) with lithio methyl acetate in amounts such that the molar ratio of 3'-O-(5-methyl-2-oxohexanoyl)-cephalotaxine to lithio methyl acetate is 1:2, the reaction being carried out in THF under anhydrous conditions in an inert atmosphere at about −78° C. to form a mixture of deoxyharringtonine and a deoxyharringtonine diastereomer; and g. separating deoxyharringtonine from the mixture resulting from step (f).

3. A process for the preparation of deoxyharringtonine comprising the following steps:

a. reacting 1-lithio-3-methylbut-1-yne with a 150% to 165% excess of the stoichiometric amount of ethyl t-butyl oxalate in THF containing an amount of a suitable hydrocarbon solvent sufficient to solubilize said 1-lithio-3-methylbut-1-yne, the reaction being carried out under anhydrous conditions in an inert atmosphere at a temperature of from 0° to 10° C. to form t-butyl 5-methyl-2-oxohex-3-ynoate;

b. adding sufficient trifluoroacetic acid to the reaction product resulting from step (a) to form 5-methyl-2-oxohex-3-ynoic acid;

c. hydrogenating 5-methyl-2-oxohex-3-ynoic acid in the presence of a catalytic amount of a suitable catalyst to form 5-methyl-2-oxohexanoic acid;

d. reacting 5-methyl-2-oxohexanoic acid with at least a 10% excess of the stoichiometric amount of oxalyl chloride under anhydrous conditions at a temperature of 25° to 60° C. for from 40 to 60 hours to form 5-methyl-2-oxohexanoyl chloride;

e. reacting cephalotaxine with a 50% to 200% excess of the stoichiometric amount of 5-methyl-2-oxohexanoyl chloride in a suitable solvent at about 25° to 30° C. for a minimum of 24 hours in the presence of a molar amount of pyridine equivalent to the initial amount of 5-methyl-2-oxohexanoyl chloride to form 3'-O-(5-methyl-2-oxohexanoyl)-cephalotaxine;

f. reacting 3'-O-(5-methyl-2-oxohexanoyl)-cephalotaxine contained in the reaction mixture resulting from step (e) with lithio methyl acetate in amounts such that the molar ratio of 3'-O-(5-methyl-2-oxohexanoyl)-cephalotaxine to lithio methyl acetate is 1:2, the reaction being carried out in THF under anhydrous conditions in an inert atmosphere at about −78° C. to form a mixture of deoxyharringtonine and a deoxyharringtonine diastereomer; and g. separating deoxyharringtonine from the reaction mixture resulting from step (f).

4. The composition 3'-O-(5-methyl-2-oxohexanoyl)-cephalotaxine having the following general structure:

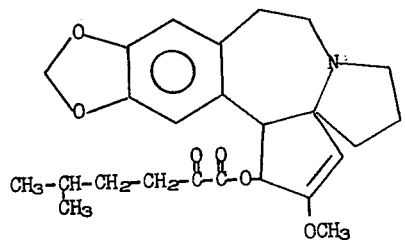

said composition being characterized by having an infrared spectrum which includes a peak at 1725 cm$^{-1}$, a shoulder at 1730 cm$^{-1}$, and peaks at 1645 cm$^{-1}$ and 935 cm$^{-1}$; an nmr spectrum at 100 MHz which includes δ 0.81 (d, J = 6 Hz, 6H), δ 3.68 (s, 3H), δ 3.81 (d, J = 10 Hz, 1H), δ 5.08 (s, 1H), δ 5.82 (s, 2H), δ 5.86 (d, J = 10 Hz, 1H), and δ 6.56 and δ 6.58 (2s, 1H each); and high-resolution mass spectrum which shows that M$^+$ = 441.215.

* * * * *